United States Patent [19]
Hoftman

[11] Patent Number: 5,658,077
[45] Date of Patent: Aug. 19, 1997

[54] SPONGE COUNTING BAG

[76] Inventor: Moshe M. Hoftman, 9410 DeSoto Ave., Chatsworth, Calif. 91311

[21] Appl. No.: 404,285

[22] Filed: Mar. 14, 1995

[51] Int. Cl.⁶ ............................................. B65D 33/20
[52] U.S. Cl. ........................ 383/35; 383/37; 383/87; 383/211; 206/362
[58] Field of Search .................... 383/35, 2, 37, 383/87, 210, 211; 206/362

[56] References Cited

U.S. PATENT DOCUMENTS

| | | | |
|---|---|---|---|
| 2,197,113 | 4/1940 | Piazze | 383/35 |
| 3,070,280 | 12/1962 | Richmond | 383/211 |
| 3,113,715 | 12/1963 | Pangrac | 383/35 |
| 3,224,574 | 12/1965 | McConnell et al. | 383/35 |
| 3,310,225 | 3/1967 | Hoblit et al. | 383/211 |
| 3,448,555 | 6/1969 | Shabram | 383/37 |
| 3,749,237 | 7/1973 | Dorton | 206/438 |
| 3,760,940 | 9/1973 | Bustin | 383/35 |
| 3,979,050 | 9/1976 | Cilia | 383/35 |
| 4,234,086 | 11/1980 | Dortoy | 383/37 |
| 4,361,231 | 11/1982 | Patience | 206/362 |
| 4,758,099 | 7/1988 | Branson | 383/35 |
| 4,785,940 | 11/1988 | Wilson | 383/211 |
| 4,846,586 | 7/1989 | Bruno | 383/35 |
| 5,048,683 | 9/1991 | Westlake | 206/362 |
| 5,429,234 | 7/1995 | Bohannon | 206/362 |

Primary Examiner—Stephen P. Garbe

[57] ABSTRACT

The sponge counting bag is formed of front and back sheets of transparent polymer material which are joined at the edges and bottom to form an open-topped bag. The back sheet extends above the front sheet. The front sheet is folded down to form a cuff, and the lower edge of the cuff is stretched to form wrinkles whereby the lower edge hangs outwardly away from the bag so that the cuff can be manipulated easily to pull the bag open. In one species, the top of the back sheet forms a flap which can be folded down to cover the otherwise open top. This flap is detachably, adhesively attached so that the bag normally remains closed, but can be reopened if necessary. Another species has a plurality of cuffed bags arranged one above the other so that the plurality can be hung from one support.

5 Claims, 2 Drawing Sheets

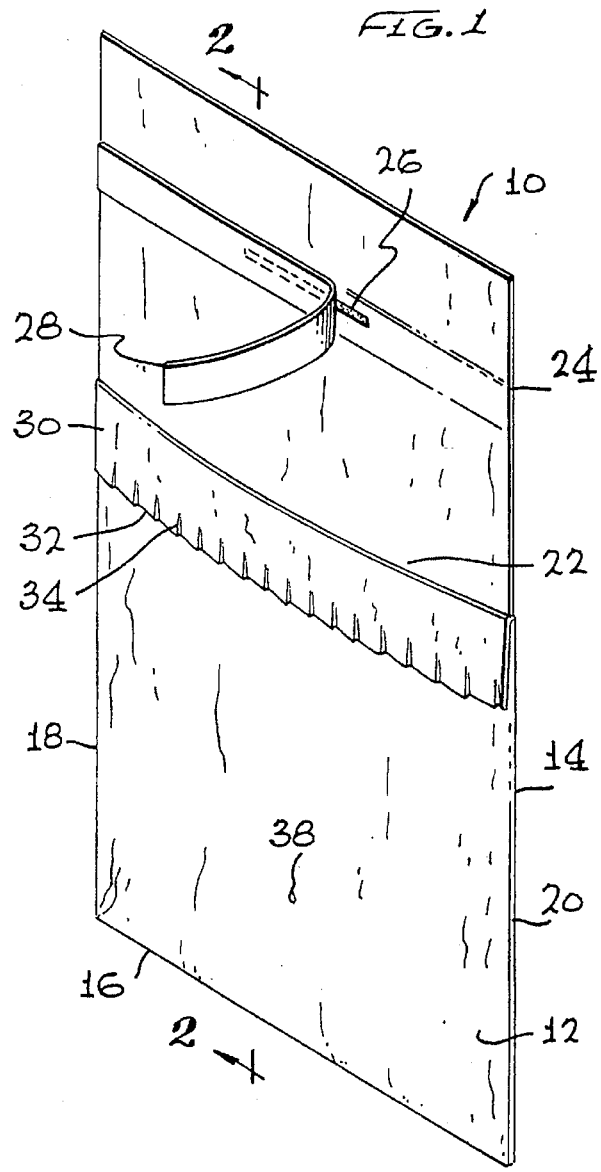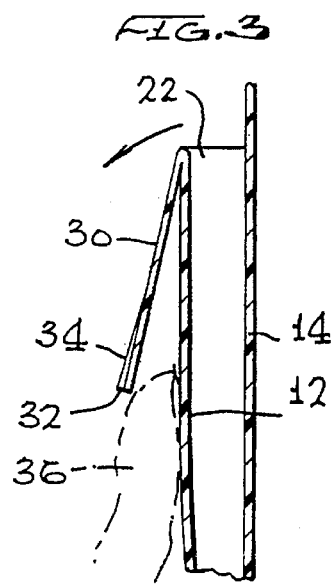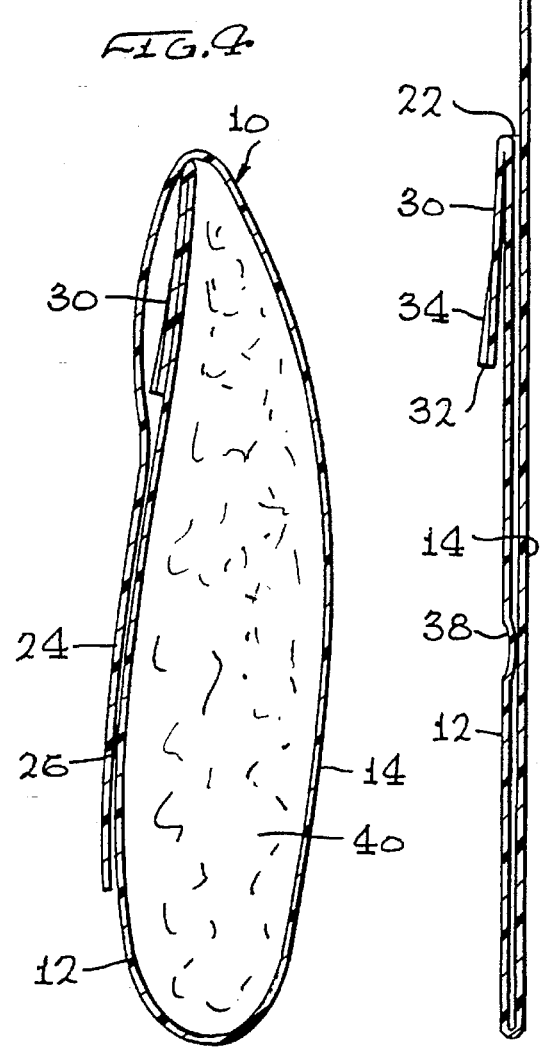

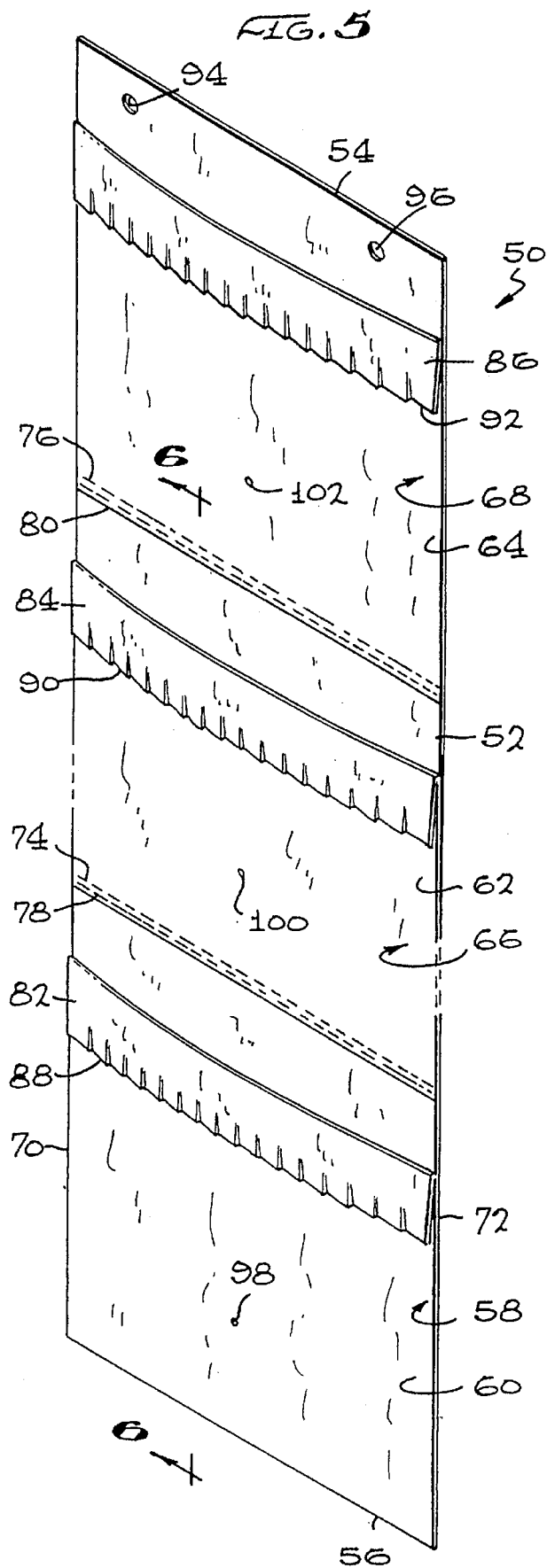
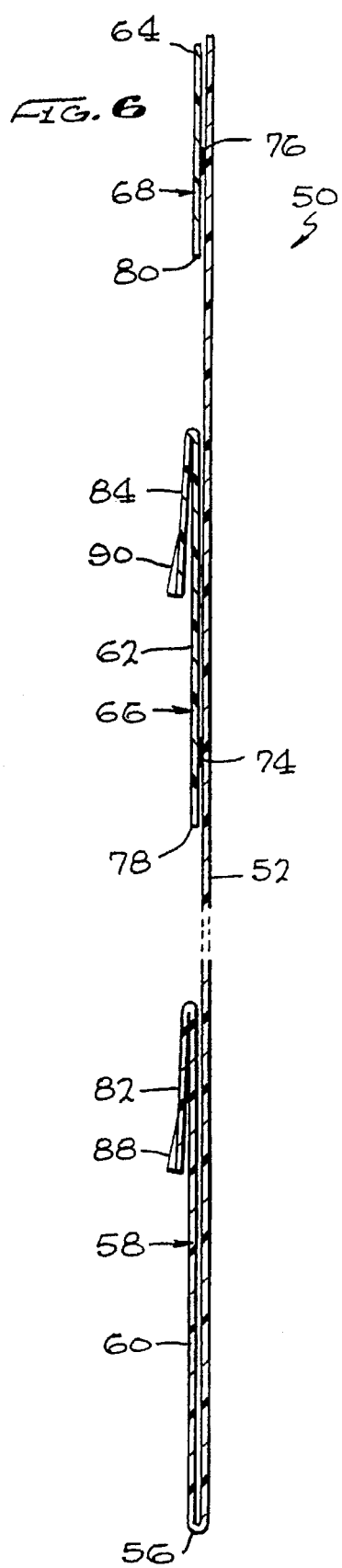

SPONGE COUNTING BAG

FIELD OF THE INVENTION

This invention is directed to a sponge counting bag for use in operating rooms to receive and retain used sponges so that they may be readily counted before destruction.

BACKGROUND OF THE INVENTION

Many sponges are used in surgical operations. The use includes placement in the body cavity through a surgical opening. This use is for the purpose of controlling bleeding and managing other fluid so that the surgical field remains accessible. It is very important that the sponges be removed before closure of the surgical opening. To assure that all are removed, it is present practice to count the total number of sponges at the time of closure. In order to aid in this counting procedure, plastic bags are presently used. However, the present plastic bags are inconvenient and difficult to use, especially with a gloved hand. Thus, there is need for improved equipment for counting sponges.

SUMMARY OF THE INVENTION

In order to aid in the understanding of this invention, it can be stated in essentially summary form that it is directed to a sponge counting bag which is formed of front and back sheets of substantially transparent-synthetic polymer composition material. The front and back sheets are closed at the bottom and side edges. The back sheet extends upward, and the front sheet is folded down at its top edge to form a cuff. The cuff is wrinkled on its free edge to permit easy opening of the bag. The sponge counting bag may have a reopenable, fold-down flap or may have a plurality of such bags arranged one above the other.

It is thus a purpose and advantage of this invention to provide a sponge counting bag which is easy to open so that sponges can be readily placed therein at the end of a surgical procedure so that they may be readily counted.

It is a further object and advantage of this invention to provide a sponge counting bag which facilitates placement of the sponges in the counting bag for subsequent counting by having a cuff thereon which is readily grasped or single-finger manipulated to pull the bag open.

It is a further purpose and advantage of this invention to provide a flap on the sponge counting bag which can releaseably close the bag.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

FIG. 1 is an isometric view of the first preferred embodiment of the sponge counting bag of this invention.

FIG. 2 is an enlarged section taken generally along line 2—2 of FIG. 1.

FIG. 3 is an enlarged section of a portion of the bag shown in FIG. 2 showing the easy manipulation of the wrinkled edge.

FIG. 4 is a section similar to FIG. 2 showing the bag filled with sponges and showing its flap closed.

FIG. 5 is an isometric view of the second preferred embodiment of the sponge counting bag of this invention, with parts broken away.

FIG. 6 is an enlarged section taken generally along the line 6—6 of FIG. 5, with parts broken away.

DESCRIPTION OF THE PREFERRED EMBODIMENTS

The first preferred embodiment of the sponge counting bag of this invention is generally indicated at 10 in FIGS. 1, 2 and 4. The bag 10 is made of substantially transparent flexible synthetic polymer composition sheet material such as polyethylene. The bag has a front layer 12 and a back layer 14. These layers are attached together along bottom edge 16 and left and right edges 18 and 20 to create a bag having an opening 22 at its top. The back layer extends upward above the bag opening to form closure flap 24. The closure flap has a height almost as tall as the bag from its bottom edge to its opening so that the closure flap can be pulled down over the front for substantial overlap over the bag opening.

A line of pressure sensitive adhesive 26 is provided on the front of the flap 24. The line of adhesive is covered by protective release strip 28. The release strip 28 covers the adhesive 26 until adhesive closure of the bag is desired, whereupon the release strip is removed. It is shown half pulled off in FIG. 1. After it is removed, the flap is pulled down over the front of the bag and is attached closed by means of the pressure sensitive adhesive, as seen in FIG. 4. The adhesive is of such nature as to be sufficiently aggressive to securely hold down the closure flap to hold the bag closed under ordinary circumstances. However, the aggressiveness of the adhesive is sufficiently limited so that, if it is required that the bag be reopened, such can be accomplished without tearing the bag. After closure, if the closure flap is lifted, the bag can be opened without tearing.

Another important feature of the bag 10 is the folding down of the upper edge of the front layer to form folded-down flap or cuff 30. The cuff 30 is stretched along its lower edge 32 to form wrinkles 34. The wrinkles can be achieved by any convenient means such as by hot corrugated rollers or by direct application of heat, such as infrared or laser application. In this latter case of the application of heat, the polymer material is such that, when heat is applied, wrinkling occurs. Since there are wrinkles adjacent the lower edge of the cuff, this lower edge cannot lie directly flat against the front layer 12. As a consequence, a finger 36 can readily engage under the cuff 30 to pull open the opening 22 seen in FIG. 3. The wrinkling prevents the inconvenience and delay which sometimes occurs when two polymer layers must be separated.

The sponge counting bag 10 has a tack seal 38 between its front and back layers, see FIGS. 1 and 2. This tack seal is substantially midway between the left and right edges 18 and 20. The tack seal is about one-third the way up the bag 10 between its bottom edge 16 and opening 22. The tack seal is not a very localized one, but may be a ring to spread the sealing. The tack seal is configured so that it holds the front and back together moderately well but, when a larger bag volume is required, the tack seal can be pulled apart without making an opening in the front or back layers of the bag.

When the sponge counting bag 10 is in use, it is held up by the top edge of the closure flap 24 in the open position shown in FIGS. 1 and 2. When the sponges are small, the tack seal 38 is left attached. Five small sponges can be placed in an upright column on each side of the tack seal. Thus, the tack seal holds the columns of sponges in line for recounting even after the bag is closed. However, when the sponges are larger, larger bag volume is required so that the tack seal is pulled apart.

Sponges 40 are placed in the bag to a determined count until the bag is full, as seen in FIG. 4. When full, the release strip 28 is removed and the closure flap is pulled down and sealed. If a recount is necessary, just prior to closing of the operating incision by the surgeon, the sponges in the bag can be counted through the transparency thereof, or if there are several layers, the bag can be reopened by pulling open the flap so that the individual sponges can be separated, counted and replaced into the bag. This permits easy recounting and easy resealing.

A second preferred embodiment of the sponge counting bag of this invention is shown in FIGS. 5 and 6 where it is generally indicated at 50. The sponge counting bag 50 comprises a plurality of attached bags arranged one above the other. The sponge counting bag 50 comprises a back layer 52 of flexible substantially transparent, thermoplastic synthetic polymer composition material, such as polyethylene. In the original manufacture of the sponge counting bag 50, the back layer is folded up all the way to the back top edge 54. The bottom fold 56 closes the bottom of the lowermost sponge bag 58 of the upright string of sponge counting bags. The folding up of the back layer provides front layer 60, front layer 62, and front layer 64, respectively, of the lower sponge bag 58, the intermediate sponge bag 56 and the upper sponge bag 68. The three sponge bags illustrated are sealed at their left and right edges 70 and 72 by heat sealing. In addition, the lower closure of the intermediate and upper sponge bags 66 and 68 are formed by heat-sealing along heat seal bottom edge lines 74 and 76. The openings of the lower and intermediate bags 58 and 66 are created by slitting the front layer at slit lines 78 and 80. This creates flaps or cuffs 82 and 84. These cuffs are folded down, as shown. They may have to be separated at their edges for proper folding. The top edge of the front sheet is also folded down at the upper sponge bag to create flap or cuff 86. It may be necessary to reheat-seal the edges of these cuffs in order to hold them down, as shown. The cuffs are wrinkled along their lower, free edge. Wrinkles 88, 90 and 92 are shown. These wrinkles permit easy opening of each of the bags, as desired. The entire bag system 50 is retained in place by hanging it from convenient hooks which engage in support holes 94 and 96. The set of bags 50 also has tack seals, 98, 100 and 102 for the same purpose as the tack seal 38.

The system of sponge counting bags 50 is used in much the same manner as the use of the sponge counting bag 10. The system of bags 50 is supported from suitable hooks engaging in its support holes near the top edge. Each of the individual bags is then positioned for accessibility. When a used sponge is received, the nurse places it in one of the bags. This is accomplished by slipping a finger under the wrinkled edge which opens that bag without difficulty. This provides ease and speed of operation. The sponges in the bags are visible so that they may be counted at the end of the surgical procedure.

This invention has been described in its presently contemplated best modes, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A sponge counting bag comprising:

a front layer and a back layer of flexible synthetic polymer composition sheet material, at least said front layer being substantially transparent, said front layer and said back layer being attached to each other to form a left edge, bottom edge and right edge of said bag, leaving its top open, said back layer extending above the open top of said bag, said front layer being folded downward from said open top of said bag to define a cuff having a downwardly directed edge, said cuff being wrinkled so that said cuff does not lie completely flat against said front layer so that said cuff can be readily engaged to pull said front layer away from said back layer to open said bag, said back layer being sufficiently long so that it can be folded down below said cuff to close said bag; and a tack seal between said front layer and said back layer positioned so that said tack seal limits the opening of said bag, said tack seal being sufficiently soft so that said tack seal can be broken away for full access to the interior of said bag without perforating said bag.

2. The sponge counting bag of claim 1 wherein said cuff of said bag that is wrinkled so that said cuff does not lie flat against said front layer.

3. A sponge counting bag comprising:

a front layer and a back layer of flexible synthetic polymer composition sheet material, at least said front layer being substantially transparent, said front layer and said back layer being attached to each other to form a left edge, bottom edge and right edge of said bag, leaving its top open, said front layer extending above the open top of said bag;

a tack seal between said front layer and said back layer substantially in the middle of each said bag to permit said bag to be held closed for receipt of small sponges, said tack seal being separable so as to permit said bag to open farther for the receipt and counting of large sponges;

said front layer being folded downward from said open top of said bag to define a cuff having a downwardly directed edge, said cuff being wrinkled so that said cuff does not lie completely flat against said front layer so that said cuff can be readily engaged to pull said front layer away from said back layer to open said bag; and said back layer extending sufficiently high so that, when said back layer is brought down over the front of said bag to close said bag, said back layer reaches said front layer below said cuff to permit attachment of said back layer to said front layer below said cuff.

4. A sponge counting bag comprising:

a front layer and a back layer, said layers being formed of substantially transparent flexible synthetic polymer composition sheet material, said layers having a bottom edge and left and right edges, said layers being attached together at said bottom edge and said left and right edges so as to form an open-top bag with a front surface;

said front and back layers of said bag having a tack seal therebetween substantially equidistant between said right and left edges so that said front and back layers are held close to each other for ease of counting small sponges, said tack seal being separable to permit said counting bag to open farther to permit the receipt and counting of larger sponges; and said back layer extending above the open top of said bag to define a closure flap with a facing surface, said front layer being folded down at said open top of said bag to form a cuff having a downwardly directed lower edge, said cuff being wrinkled so that said cuff does not lie flat against said front layer, said closure flap of said back layer extending sufficiently high so that, when it is brought down over said open top of said bag, it extends downward below said cuff so that said surfaces face each other, pressure sensitive adhesive on only one of said surfaces, said pressure sensitive adhesive extending only partially across said one surface to minimize adhesive transfer to the gloves of a person reopening said bag for sponge recounting.

5. A sponge counting bag comprising:

a front layer and a back layer, said layers being formed of substantially transparent flexible synthetic polymer composition sheet material, said layers having a bottom edge and left and right edges, said layers being attached together at said bottom edge and said left and right edges so as to form an open-top bag with a front surface;

said front and back layers of said bag having a tack seal therebetween substantially equidistant between said right and left edges so that said front and back layers are held close to each other for ease of counting small sponges, said tack seal being separable to permit said counting bag to open farther to permit the receipt and counting of larger sponges;

said back layer extending above the open top of said bag to define a closure flap with a facing surface, said front layer being folded down at said open top of said bag to form a cuff having a downwardly directed lower edge, said cuff being wrinkled so that said cuff does not lie flat against said front layer, said closure flap of said back layer extending sufficiently high so that, when it is brought down over said open top of said bag, it extends downward below said cuff so that said surfaces face each other, pressure sensitive adhesive on only one of said surfaces, said pressure sensitive adhesive extending only partially across said one surface to minimize adhesive transfer to the gloves of a person reopening said bag for sponge recounting; and a release strip covering said pressure sensitive adhesive, said pressure sensitive adhesive being sufficiently aggressive to attach said closure flap to said front layer below said cuff and said pressure sensitive adhesive being sufficiently non-aggressive so that said closure flap can be pulled loose for reopening said bag for recounting of sponges in said bag.

* * * * *